United States Patent [19]

Chester et al.

[11] Patent Number: 5,538,129
[45] Date of Patent: Jul. 23, 1996

[54] PACKAGE FOR ADHESIVE PRECOATED DENTAL APPLIANCE

[75] Inventors: Bruce E. Chester, Irvine; James D. Cleary, Glendora; Evangelos G. Georgakis, Altaloma; Russell A. Jordan, Rancho Cucamonga; Kenneth E. Hoevel, Monrovia; Randall E. Adam, Sierra Madre, all of Calif.

[73] Assignee: Minnesota Mining and Manufacturing Company, St. Paul, Minn.

[21] Appl. No.: 407,190

[22] Filed: Mar. 21, 1995

[51] Int. Cl.$^6$ .......................... B65D 83/10; A61B 19/02
[52] U.S. Cl. .......................... 206/63.5; 206/469; 206/813
[58] Field of Search .................. 206/438, 63.5, 206/368, 460, 461, 467, 469, 813

[56] References Cited

U.S. PATENT DOCUMENTS

| | | | |
|---|---|---|---|
| 3,343,669 | 9/1967 | Loran | 206/63.5 |
| 3,924,748 | 12/1975 | Braverman | 206/534.1 |
| 4,055,672 | 10/1977 | Hirsch et al. | 426/127 |
| 4,231,477 | 11/1980 | De Felice | 206/469 X |
| 4,251,712 | 2/1981 | Parr | 219/203 |
| 4,355,721 | 10/1982 | Knott, II et al. | 206/524.2 |
| 4,416,375 | 11/1983 | Braverman et al. | 206/534.1 |
| 4,537,305 | 8/1985 | Takanashi | 206/438 |
| 4,587,152 | 5/1986 | Gleichenhagen et al. | 428/195 |
| 4,735,318 | 4/1988 | Keffeler | 206/532 |
| 4,848,066 | 7/1989 | Luhman | 53/485 |
| 4,898,276 | 2/1990 | Georgakis | 206/369 |
| 4,977,003 | 12/1990 | Brown et al. | 428/35.5 |
| 4,978,007 | 12/1990 | Jacobs et al. | 206/469 |
| 4,979,611 | 12/1990 | Bolliger et al. | 206/83 |
| 5,015,180 | 5/1991 | Randklev | 433/9 |
| 5,139,188 | 8/1992 | Scharf | 224/217 |
| 5,172,809 | 12/1992 | Jacobs et al. | 206/368 |
| 5,221,202 | 6/1993 | James | 206/63.5 X |
| 5,236,108 | 8/1993 | House | 222/541 |
| 5,328,363 | 7/1994 | Chester et al. | 433/9 |
| 5,348,154 | 9/1994 | Jacobs et al. | 206/369 |
| 5,350,059 | 9/1994 | Chester et al. | 206/63.5 |
| 5,354,199 | 10/1994 | Jacobs et al. | 433/9 |
| 5,429,229 | 7/1995 | Chester et al. | 206/63.5 |

FOREIGN PATENT DOCUMENTS

WO91/06257  10/1989  WIPO.

OTHER PUBLICATIONS

"Could These Be New Containers", *Packaging*, Apr. 1994, p. 32.

*Primary Examiner*—Jacob K. Ackun
*Attorney, Agent, or Firm*—Gary L. Griswold; Walter N. Kirn; James D. Christoff

[57] ABSTRACT

A package for an adhesive precoated dental appliance such as an orthodontic bracket includes a container having a well and a flange, and a cover that extends over an opening of the well. A pressure sensitive adhesive releasably connects the cover to the flange along a first region, and a hermetic seal extends between the cover and the flange along a second region that is located between the first region and the opening of the well. The hermetic seal cooperates with the pressure sensitive adhesive to provide a reliable, easily openable package. The hermetic seal also prevents volatile components of adhesive on the dental appliance from contacting the pressure sensitive adhesive and thereby decreases loss of the volatile components from within the package in order to extend the expected shelf life of the adhesive precoated appliance.

15 Claims, 6 Drawing Sheets

PACKAGE FOR ADHESIVE PRECOATED DENTAL APPLIANCE

BACKGROUND OF THE INVENTION

1. Field of the Invention

This invention relates to a package especially adapted for use with a dental appliance that is precoated with adhesive for direct bonding to tooth structure.

2. Description of the Related Art

Certain types of dental appliances are used with an adhesive for bonding the appliance to tooth structure. For example, orthodontic brackets typically have a base surface that is "buttered" or coated with an adhesive for bonding to a labial or lingual surface of the tooth. Such brackets are used in orthodontic treatment to serve as a handle for the tooth so that the tooth can be moved to a desired position.

Examples of recent advances in the field of direct bonded dental appliances are described in U.S. Pat. Nos. 4,978,007, 5,015,180, 5,172,809 and 5,348,154, all of which are assigned to the assignee of the present invention. U.S. Pat. No. 5,015,180 describes in one embodiment an orthodontic bracket and a light curable paste sandwiched between a base of the bracket and a flexible, releasably adhering cover sheet. To bond the bracket to a tooth, the cover sheet is removed from the paste and the bracket base is then applied to the tooth. The invention described in U.S. Pat. No. 5,015,180 represents a time savings for the orthodontic practitioner because the adhesive can be coated onto the bracket base by the manufacturer, and the practitioner need not carefully dispense and apply the adhesive to the bracket base before bonding the bracket to the tooth.

U.S. Pat. Nos. 4,978,007, 5,172,809 and 5,348,154 describe in one embodiment a container or substrate having a recess, an orthodontic bracket having an adhesive on an exterior surface, and a cover extending over the recess. Such construction is advantageous in that the adhesive in the recess is protected from light, oxygen, water vapor and contaminants. Preferably, the bracket is retained in the recess in an orientation that facilitates grasping of the bracket for direct placement onto the tooth surface.

Orthodontic brackets are available in a wide variety of configurations or prescriptions. For example, the base of the bracket may have a particular configuration that matches the contour and size of a particular tooth. In addition, the number and shape of the tiewings, the shape and size of the archwire slot, and the characteristics of other elements of the bracket may vary in accordance with the needs of the patient and the treatment technique preferred by the orthodontist. Moreover, certain specialized brackets, such as brackets with hooks or other auxiliary attachments, may be desirable in some instances. As a consequence, the orthodontist may choose to retain a wide variety of brackets on hand so that the desired brackets can be immediately selected and put into use without waiting for additional brackets to be shipped from the manufacturer.

As can be appreciated, some precoated orthodontic brackets that are ordered from the manufacturer by the orthodontist for the orthodontist's own inventory may not be used for some time after manufacture. For this reason, efforts have been made in the past to ensure that the adhesive retains its expected bonding and handling characteristics in reliable fashion over the expected shelf life of the packaged bracket. Shelf life issues relating to the adhesive are important, because an adhesive that does not properly bond the bracket to the tooth may subsequently debond in spontaneous fashion. Such an occurrence is a nuisance to both the patient and the orthodontist, since the patient must return to the orthodontist for rebonding or replacement of the bracket.

Examples of packages for adhesive precoated dental appliances such as orthodontic brackets are described in U.S. Pat. Nos. 5,328,363 and 5,350,059. Such packages include a container having a well to receive the appliance. The container includes a top flange surrounding an opening over the well, and a cover extends over the opening and the flange to initially close the well. Preferably, each appliance is individually packaged, so that certain brackets as may be needed for a particular patient can be selected, arranged in a set-up tray and carried to the patient's chair in convenient fashion. Individual packaging also helps insure that the appliance and the adhesive are not unduly exposed to the atmosphere before use.

The container and the cover for the packaged dental appliance as described in U.S. Pat. Nos. 5,328,363 and 5,350,059 are each made from a sheet of flexible material that provides a substantial barrier to the transmission of oxygen, water vapor and light having a wavelength that might otherwise cause the dental adhesive to prematurely cure. A pressure sensitive adhesive is provided to join the cover to the flange. Optionally, a repositionable adhesive can be used to enable the orthodontist to reclose the package as may be desired in certain instances.

There is a continuing need in the art to improve the shelf life of packaged, adhesive precoated dental appliances such as orthodontic brackets so that the brackets can be retained in the orthodontist's inventory for longer periods of time without adversely affecting the handling or bonding characteristics of the adhesive. Preferably, any such improvements should not add significant additional expense, should be reliable in use, and should not render the package difficult to open.

SUMMARY OF THE INVENTION

It has been found that the shelf life characteristics of adhesive precoated orthodontic brackets are significantly affected by the presence of the pressure sensitive adhesive used to join the cover to the container. It is now suspected that volatile components in the orthodontic adhesive dissolve into the pressure sensitive adhesive of prior art packages and thereby facilitate degradation of the orthodontic adhesive. Such a result is somewhat surprising, in that the pressure sensitive adhesive has long provided a secure and reliable mechanical bond between the cover and the container flange.

The present invention is directed to a packaged article that comprises a container having a well with an opening and a flange surrounding the opening, and a dental appliance having an exterior surface. An adhesive is on the exterior surface and includes one or more volatile components. A cover extends over the opening and the flange, and a pressure sensitive adhesive releasably connects the cover to the flange along a first region at least partially surrounding the opening. A hermetic seal connects the cover to the flange along a second region surrounding the opening. The second region is located between the first region and the opening for preventing at least a portion of the volatile components from substantially contacting the pressure sensitive adhesive.

A number of embodiments of the invention are possible. In one embodiment, the hermetic seal is comprised of a heat seal that joins an aluminum foil layer to the flange of the container along an annular, oval-shaped region. In turn, the heat sealed region is surrounded by a die-cut layer of pressure sensitive adhesive that is also located between the aluminum foil layer and the container flange. In another embodiment, a layer of heat seal adhesive, a layer of aluminum foil, a layer of pressure sensitive adhesive and a top lidding (optionally of label stock) are coextensive across the flange and the opening. The aluminum foil is heat sealed to the flange, and is optionally scored to facilitate tearing of the foil, such that a portion of the foil remains affixed to the top layer while remaining areas of the foil remain affixed to the flange as the cover is opened. In other embodiments, the aluminum foil is replaced with a barrier layer of other materials such as polyvinylidene chloride ("PVDC"), and the barrier layer optionally is separable from the container and the cover once the cover has been lifted from the opening for access into the well. The structure and advantages of these and other embodiments of the invention shall become better understood following a review of the accompanying drawings and the detailed description set out in the paragraphs that follow.

DETAILED DESCRIPTION OF THE PREFERRED EMBODIMENTS

Figure 1:
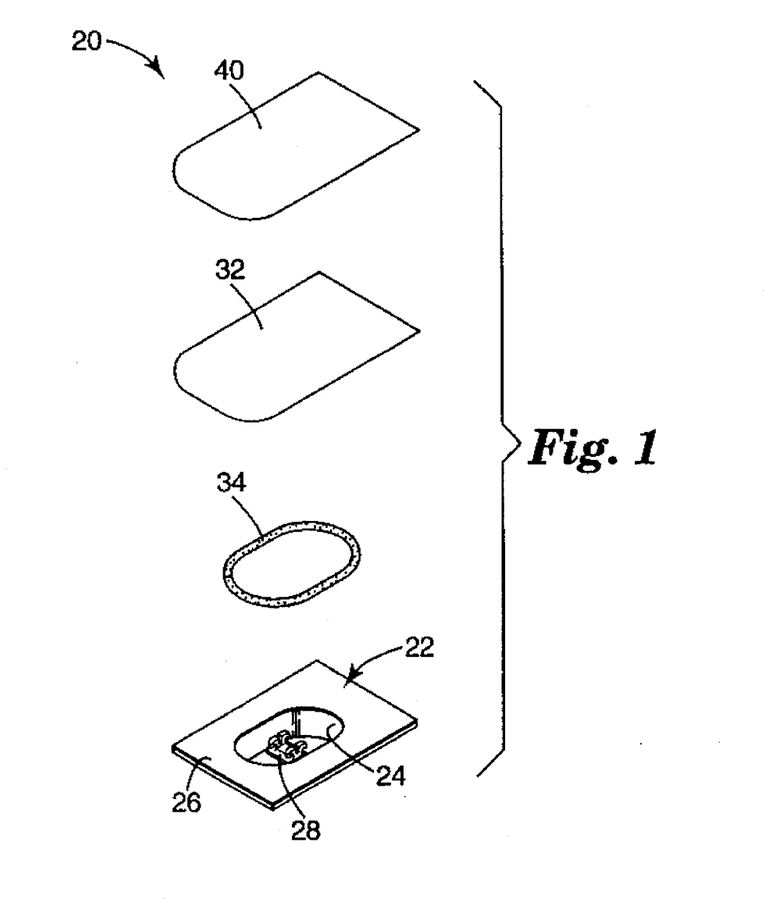
FIG. 1 is an exploded, perspective view of a packaged article constructed in accordance with one embodiment of the present invention.
Figure 2:
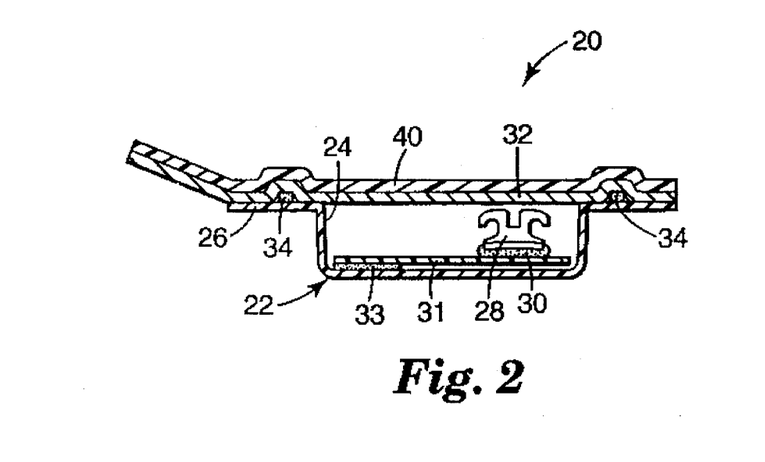
FIG. 2 is an enlarged, exaggerated scale, side cross-sectional view of the article shown in FIG. 1 as it appears once assembled.
Figure 3:
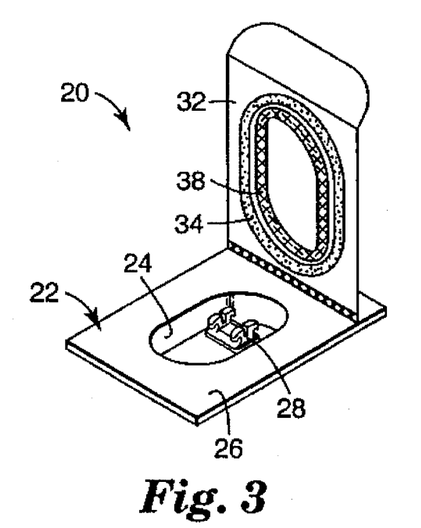
FIG. 3 is a reduced, perspective view of the article shown in FIG. 2, except that a cover of the article has been opened in order to access a dental appliance located in a container well.

A packaged article 20 constructed in accordance with one embodiment of the present invention is illustrated in FIGS. 1–3. The article 20 includes a container 22 that has an oval-shaped bottom and an upright side wall that defines an oval in plan view. The side wall and the bottom together define a well 24. A rectangular-shaped top flange 26 surrounds an upper, oval-shaped opening over the well 24 and is integrally connected to the side wall of the container 22.

The container 22 is preferably formed from a sheet of flexible material that provides a substantial barrier to the transmission of light, oxygen and water vapor. The sheet of material forming the container 22 is preferably black 0.33 mm thick polyethylene terephthalate glycol ("KODAR" brand PETG No. 6763, Kodak Chemical Company) that is treated with a silicone release agent (no. 24, Dow Chemical or no. SM2121, General Electric).

A dental appliance 28 is removably received in the well 24. The appliance 28 shown in FIGS. 1–3 is an orthodontic bracket, although other appliances are, of course, possible. For example, the dental appliance may instead be an orthodontic buccal tube, a lingual button, a dental restorative or other type of dental element that is intended for placement onto tooth structure, such as an exterior surface of the tooth.

A dental adhesive 30 is located on a portion of the surface of the appliance 28. For the orthodontic bracket appliance 28 that is illustrated in FIGS. 1–3, the adhesive 30 is precoated onto a base of the appliance 28 (see FIG. 2) for directly bonding the base to the tooth structure. Suitable adhesives are described in U.S. Pat. No. 5,354,199, which is expressly incorporated by reference herein. A presently preferred composition for the adhesive 30 includes the following components (given in weight percent): 11.45% diglycidylmethacrylate of Bisphenol A ("Bis-GMA"; from 3M Company), 7.47% ethoxylated Bisphenol A dimethacrylate ("EBDMA"; DIACRYL 101 from Akzo Chemicals Inc.), 0.06% camphorquinone ("CPQ"; a photoinitiator from Aldrich Chemical Company), 0.15% diphenyliodonium hexafluorophosphate ("$(C_6H_5)_2I^+PF_6^-$"; a catalyst from 3M Company), 0.02% butylated hydroxytoluene ("BHT"; an inhibitor from PMC Specialties), 0.24% ethyl 4-dimethylaminobenzoate ("EDMAB"; an amine from Aldrich Chemical Company), and 80.61% quartz filler (from Orthocast Manufacturing Co.) that is comminuted to a particle surface area of 2.2–2.9 m$^2$/g and silane-treated with 2.60% gamma-methacryloxypropyl trimethoxysilane (A-174, Union Carbide Corp.) based on the weight of the filler.

The dental adhesive 30 can also contain suitable adjuvants such as solvents, accelerators, absorbers, diluents, stabilizers, pigments, dyes, inorganic or organic fibrous or particulate reinforcing or extending fillers, viscosity modifiers, inhibitors, surface tension depressants, wetting aids, thixotropic agents, antioxidants, medicaments (e.g., leachable fluorides), and other ingredients well known to those skilled in the art.

The viscoelastic behavior of the adhesive 30 is determined by a consistency measurement. Consistency is measured as the spread of 1.04 g ±0.01 g of adhesive sandwiched between two 10.16×10.16 cm glass plates under a 907.2 g weight. The adhesive is delivered onto the bottom plate, then the top plate and the 907.2 g weight are gently lowered onto the adhesive. The combined mass of the top plate and the 907.2 g weight is 1027±10 g. After two minutes, the spread (diameter) of the adhesive is measured to the nearest 0.8 mm in three radial directions, and the readings are averaged. The consistency is preferably in the range of about 12 mm to 28 mm, more preferably in the range of about 21 mm to about 26 mm and most preferably in the range of about 23 mm to about 24.5 mm.

A flexible film 31 having an oval configuration is received in the well 24. The film 31 is a 0.05 mm thick sheet of fluorinated ethylene propylene copolymer ("Teflon" brand FEP No. 200C, clear, E. I. du Pont de Nemours & Company) that is etched on one side by electrostatic discharge apparatus. A front section of the etched side of the film 31 is bonded to a front section of the well bottom by an acrylic pressure sensitive adhesive 33 (No. V-29, Flexcon Company, Inc., Spencer, Mass.). The appliance 28 is carried on top of a rear section of the oval film 31, and the fluorinated ethylene propylene copolymer material provides a low adhesion surface for contact with the dental adhesive 30. Alternatively, the film 31 may be a 0.025 mm thick (or 0.01 to 0.05 mm thick) sheet of clear oriented polyester, type A that is bonded by an acrylic pressure sensitive adhesive (No. H529, Flexcon) to the well bottom.

Optionally, three raised spaced-apart bumps formed on the well bottom provide support for the rear section of the oval film in spaced relation to remaining portions of the well bottom. Further details of the film and bumps may be found in U.S. Pat. No. 5,328,363 which is expressly incorporated by reference herein. Alternatively, the adhesive 30 may contact a release material coated on the well bottom, or the appliance 28 may be suspended in the well 24.

A cover 32 extends over the flange 26 in the opening of the well 24. A front portion of the cover 32 overhangs the front portion of the flange 26 and presents an inclined tab that provides a convenient handle for grasping the cover 32. By grasping the tab, the cover 32 can be moved in an arc from its closed orientation as shown in FIG. 2 covering the well 24 and to an opened configuration as shown in FIG. 3 in order to enable access to the well 24.

The cover 32 includes a layer of paper that is bonded to a "barrier" layer. The barrier layer is made of aluminum foil or of some other material that substantially blocks passage of the volatile components of the adhesive 30. The layer of paper faces away from the well 24 (i.e., faces upwardly when viewed as oriented in FIG. 2), while the layer of aluminum foil faces toward the well 24 (i.e., faces downwardly when viewed as oriented in FIG. 2). The layer of paper and layer of aluminum foil are fixed together as a laminate (no. 15113; from Lawson Mardon Flexible, Inc.).

A pressure sensitive adhesive assembly 34 releasably connects the cover 32 to the flange 26 along a first region that at least partially surrounds the opening of the well 24. The adhesive assembly 34 is preferably a laminate that includes a high tack, non-repositionable 0.0180–0.02 mm thick layer of acrylic pressure sensitive adhesive (no. H529, Flexcon) that is fixed to the aluminum foil and paper laminate, a 0.0180–0.02 mm thick layer of low tack, repositionable acrylic pressure sensitive adhesive (no. H558, Flexcon) that releasably contacts the flange 26, and a 0.025 mm thick polyester carrier film located between the layer of nonrepositionable adhesive and the repositionable adhesive. As shown in the drawings, the adhesive assembly 34 has an oval shaped central opening that surrounds the opening of the well 24.

A hermetic seal 36 (FIG. 2) connects the cover 32 to the flange 26 along a second region (designated 38 in FIG. 3) that surrounds the opening of the well 24. The second region 38 is located between the first region (where the pressure sensitive adhesive assembly 34 releasably connects the cover 32 to the flange 26) and the opening to the well 24. The hermetic seal 36 substantially prevents at least a portion of volatile components of the adhesive 30 on the appliance 28 from contacting the adhesive assembly 34.

A layer of hot melt adhesive extends along the underside surface of the aluminum foil layer. The hermetic seal 36 is made by pressing a heated, annular, oval-shaped face of a platen onto the paper and aluminum foil laminate along the second region 38. As the platen presses the paper and aluminum foil laminate into firm contact with the flange 26 of the container 22 within the oval-shaped opening of the pressure sensitive adhesive assembly 34, the hot melt adhesive is softened. Subsequently, the platen is moved away from the paper and aluminum foil laminate to enable the hot melt adhesive to cool and thereafter mechanically fix as well as hermetically seal the aluminum foil to the flange 26.

When the container 22 is opened by moving the cover 32 from its closed orientation as shown in FIG. 2 and to its open orientation as shown in FIG. 3, the hermetic seal 36 ruptures, and the repositionable adhesive of the pressure sensitive adhesive assembly 34 detaches from the flange 26. If desired, the packaged article 20 may subsequently be reclosed by moving the cover 32 toward its orientation shown in FIG. 2 so that the repositionable adhesive again contacts the flange 26 to thereafter retain the cover 32 in its closed orientation.

Preferably, a top lidding 40 is joined to the cover 32 to provide rigidity and stiffness and also to present a printable top surface. A preferred top lidding 40 is made of a 0.13 mm thick opaque white polyester film (Melanex no. 329; from ICI) that is secured to the cover 32 by a 0.025 mm thick layer of pressure sensitive adhesive (Scotch no. 9447 laminating adhesive; from 3M). The lidding 40 is affixed to the cover 32 after the heat sealing operation is completed, and as shown in the drawings the lidding 40 has the same shape as the shape of the cover 32.

The platen also includes a heated rectangular face that engages a rear section of the cover 32 when the oval-shaped platen face contacts the cover 32. The rear section is located rearwardly of the pressure sensitive assembly 34, and is heat-sealed by the rectangular face of the platen to an underlying, similarly-shaped section of the flange 26 to help insure that the cover 32 and the top lidding 40 do not completely detach from the flange 26 when the cover 32 and the lidding 40 are opened.

For the heat sealing operation, the flange 26 is preferably placed upon an aluminum pad or a resilient pad (such as a 70 durometer 0.03 in. (0.8 mm) thick silicone rubber pad) to provide support for the container 22. The platen temperature, the pressure of the platen against the cover 32 and time interval that the platen is held under pressure against the cover 32 are parameters that can be varied as may be needed to establish a satisfactory hermetic seal. As an example, the platen temperature may be about 365° F. (185° C.) when held against an array of ten covers 32 for about 2–3 seconds with a pressure of about 500 lbs (227 kg). As another example, the platen temperature may be about 80° C. and held against the lidding 175 with a pressure of about 1.5 to 2.0 kg/cm$^2$.

The top lidding 40 and the cover 32 include a line of perforations 41 that extends across the rear section of the cover 32. When the cover 32 and top lidding 40 are moved to an open, upstanding position, the cover 32 and the top lidding 40 bend at the perforations 41 in order to facilitate self-retention of the cover 32 and the top lidding 40 in their open, upright position. The perforations 41 also provide tactile feedback to the user that the cover 32 and top lidding 40 are open so that the user does not continue to pull on the cover 32 and top lidding 40 and separate the same from the container 22.

Optionally, one or more of the perforations 41 is replaced with a staked connection wherein an elongated portion of the cover 32 and the top lidding 40 are firmly pressed into an underlying portion of the flange 26 to establish a mechanical interlock. The staked connection further helps insure that the cover 32 and the top lidding 40 do not completely detach from the flange 26 when the cover 32 and the lidding 40 are opened.

The hermetic seal 36 substantially prevents volatile components in the adhesive 30, such as EDMAB and CPQ, from substantially contacting the pressure sensitive adhesive assembly 34 upon volatilization once the appliance 28 is placed in the well 24 and the cover 32 is in its closed orientation as shown in FIG. 2. EDMAB and CPQ are critical components of the appliance adhesive 30, and the loss of sufficient amounts of EDMAB and CPQ from the adhesive 30 may cause the adhesive 30 to be noticeably drier and/or stiffer. If the adhesive 30 is too stiff, it may be difficult to slide the appliance 28 on the tooth (after being initially placed on the tooth) in order to move the appliance 28 to its desired final position with precision. A dry or stiff adhesive may also result in a bond having insufficient strength when an attempt is made to bond the appliance 28 to a tooth. While a certain amount of the curatives will initially volatilize into the interior space of the well 24 once the precoated appliance 28 is placed in the container 22 and the cover 32 is closed, the hermetic seal 36 will enable the volatilization of such components to stabilize and reach equilibrium after a short period of time such that little, if any, additional loss of such components occurs until the cover 32 is opened.

Preferably, the percentage weight loss of the components EDMAB and CPQ is each less than 85%, more preferably is each less than 70%, and most preferably is each less than 60% of their original, respective weights once the precoated appliance 28 has been placed in the well 24 and the cover 32 is closed for a period of five weeks in an accelerated aging test that is conducted at 60° C. The volatilization of EDMAB and CPQ stabilizes in the closed container 22 before the weight percentage of such components remaining in the adhesive 30 decreases below a certain value which could be considered a minimum effective concentration. Below the minimum effective concentration, the adhesive 30 is considered unduly dry or stiff and may fail to provide satisfactory bond strength once the appliance 28 is bonded to the tooth.

Advantageously, the combination of the heat sealed hermetic seal 36 with the pressure sensitive adhesive assembly 34 also provides mechanical advantages in addition to the aforementioned advantage of stabilizing loss of volatile components of the dental adhesive 30. More particularly, the combination of the hermetic seal 36 with the pressure sensitive adhesive assembly 34 provides a reliable mechanical bond between the cover 32 and the flange 26 that enables the package to be opened easily and with a relatively predictable force. In the present invention, the heat seal may be relatively narrow in width (i.e., in directions across the top of the flange 26 radially away from the opening to the well 24) because one can rely on the pressure sensitive assembly 34 rather than the hermetic seal 36 to provide the majority of the bond strength between the cover 32 and the flange 26. In this regard, it should be noted that a relatively wide heat seal may be strong, but such a strong seal may be difficult to separate when opening the package. Moreover, manufacturing variabilities inherent in a heat sealing operation may render some packages having a relatively wide heat seal difficult to open.

In the embodiment described in connection with FIGS. 1–3, the hermetic seal 36 includes the portion of the hot melt adhesive that extends along the second region 38 and heat seals the aluminum foil barrier layer to the flange 26. Other constructions are also possible. For example, the barrier layer may be hermetically sealed to the flange 26 by an ultrasonic, radiant, impulse or induction sealing operation. The hot melt adhesive may be replaced with another type of hermetic seal-forming adhesive, or entirely omitted and replaced by a welding or other type of joining operation. The aluminum foil may be replaced with other films that substantially prevent passage of volatile components in dental adhesives, such as a film made of polyvinylidene chloride (that is optionally coated with a metallic material). Furthermore, the barrier layer may be considered as part of the hermetic seal that lies between the opening to the well 24 and the pressure sensitive adhesive assembly 34.

Figure 4:
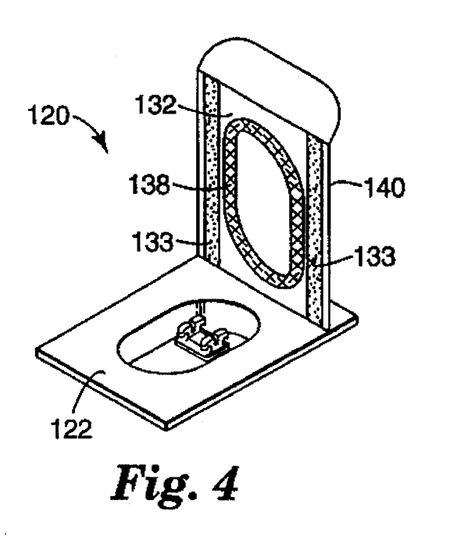
FIG. 4 is a view somewhat similar to FIG. 3, except in accordance with another embodiment of the invention.

A packaged article 120 according to another embodiment of the invention is illustrated in FIG. 4. The article 120 includes a container 122 (that is identical to the container 22 mentioned above), a cover 132, a top lidding 140, and a hermetic seal that extends in an oval along a region 138. The region 138 surrounds the opening to the well of the container 122 and is made by heat sealing the cover 132 to the container flange. The article 120 also includes two straight, spaced apart, parallel sections of pressure sensitive adhesive 133 that extend along peripheral, opposed side portions of the cover 132.

The adhesive sections 133 may be repositionable or nonrepositionable adhesive. Optionally, each adhesive section 133 is made of the three layer laminate described in connection with the adhesive assembly 34 that includes the high tack, non-repositionable acrylic pressure sensitive adhesive, the polyester carrier film and the low tack, repositionable acrylic pressure sensitive adhesive. The cover 132 may be polyester label stock (that is optionally metallized). Optionally, the cover 132 may be constructed by placing an adhesive coated polyester film (such as a repositionable "SCOTCHMARK" brand lidding, e.g., No. 7818, from 3M) over a narrower lidding section of a polyester carrier coated with a heat seal hot melt adhesive (such as "SCOTCHPAK" brand lidding, Nos. 112, 113 or 122, from 3M), so that edge sections of the cover 132 present exposed portions of pressure sensitive adhesive for releasable contact with the flange of the container 122.

Another variation to the packaged article 120 shown in FIG. 4 is constructed by replacing the narrow rectangular lidding section carrying the hot melt adhesive with a lidding section having a different configuration. For example, an oval-shaped or hexagonal-shaped section may be used. In such instances, at least a portion of the upper section of the cover 132 extends beyond the underlying lidding section in order to present one or more areas of pressure sensitive adhesive sections for contact with the container flange.

Figure 5:
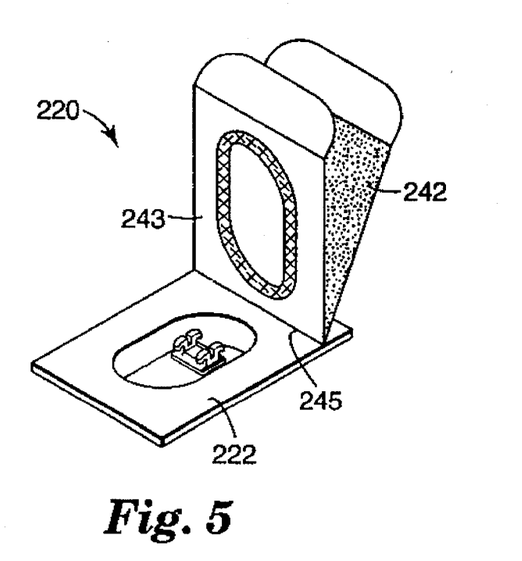
FIG. 5 is a view somewhat similar to FIGS. 3 and 4, except in accordance with yet another embodiment of the invention.

FIG. 5 illustrates a packaged article 220 in accordance with another embodiment of the invention. The article 220 includes a container 222 substantially identical to container 22, and also includes a cover 242 made of die cut lidding (such as a repositionable SCOTCHMARK brand lidding, e.g., no. 7818; from 3M) that is preferably provided with a repositionable pressure sensitive adhesive facing the flange of the container 222. A barrier film 243 (such as aluminum foil or metallized PVDC) is coextensive with the cover 242 and carries a heat sealable hot melt adhesive facing the top flange of the container 222. The film 243 is heat-sealed to the container 222 along as oval-shaped region surrounding the container well to provide a hermetic seal.

To open the packaged article 220, the user grasps the tab portions of both the barrier film 243 and the cover 242 simultaneously to pull the cover 242 and barrier film 243 away from the container 222. If closing of the article 220 is desired, the film 243 is separated from the container 222 by peeling the film 243 from the cover 242. The film 243 is then disposed of and the pressure sensitive adhesive on the cover 242 is then pressed onto the top flange of the container 222. The film 243 is either torn along the hinge line (designated 245), or is constructed shorter than the cover 242 so that the film 243 does not extend past the hinge line 245 and is instead completely removed before the cover 242 is re-closed.

Figure 7:
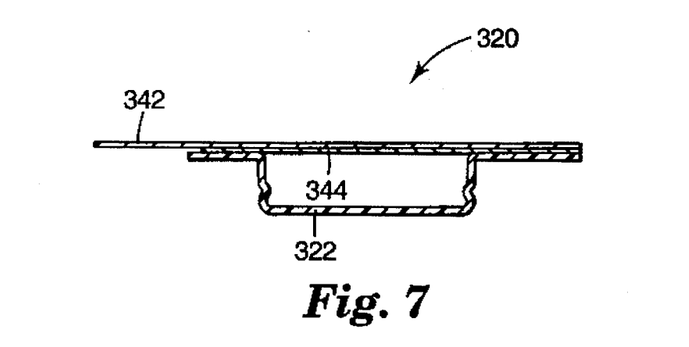
FIG. 7 is a side cross-sectional view of the article shown in FIG. 6.
Figure 8:
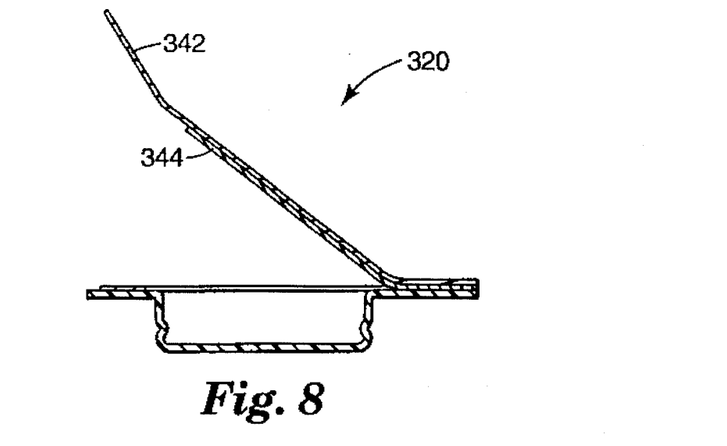
FIG. 8 is a view somewhat similar to FIG. 7 except that a cover of the article has been opened.
Figure 9:
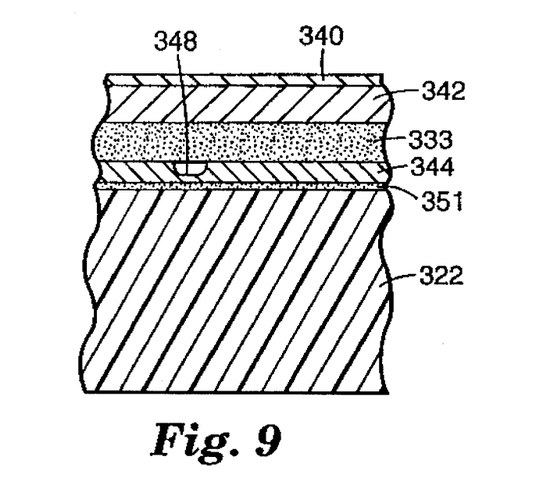
FIG. 9 is an enlarged side cross-sectional view of a portion of the article illustrated in FIG. 7.

The packaged article 320 that is shown in FIGS. 6–9 includes a container 322 that is substantially identical to the container 22. A layer of aluminum foil 344 extends over the well and flange of the container 322, and is affixed to the flange by a hot melt heat seal adhesive 351 (see the enlarged view in FIG. 9). The foil layer is embossed or scored (as shown in detail in FIG. 7) to provide two lines of weakness 346, 348 that are illustrated in FIG. 9.

The line of weakness 348 is generally U-shaped and extends about a front portion and two side portions of the opening of the well. The line of weakness 346 extends in a somewhat truncated V-shaped pattern between the line of weakness 348 and the front, overhanging tab of the cover 342 provided for grasping. The cover 342 is fixed to the aluminum foil layer 344 by a pressure sensitive adhesive 333 (preferably, an acrylic repositionable pressure sensitive adhesive). Preferably, the cover 342 includes a printable surface so that identification of the contents of the well and other information (such as lot codes and suggested shelf life or expiration dates) are provided.

Figure 6:
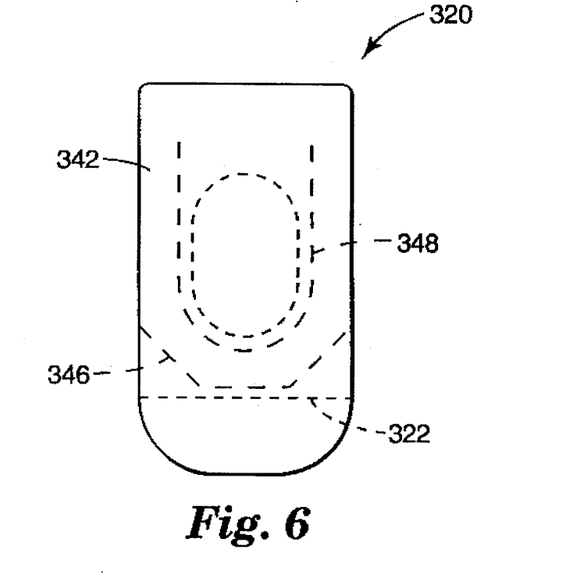
FIG. 6 is a plan view of a packaged article in accordance with still another embodiment of the invention.

When the cover 342 is moved from its closed position as shown in FIGS. 6–7 and opened as indicated by the arrow in FIG. 8, the foil layer 342 ruptures along the line of weakness 348. The portion of the foil layer 344 that is located radially outwardly from the line of weakness 348 remains affixed (due to the heat seal) to the flange of the container 322 and detaches from the pressure sensitive adhesive 333 as the cover 342 is raised, while a U-shaped central portion of the foil layer 344, namely the portion of the foil layer 344 extending over the well, remains affixed to the cover 342. In this manner, the well is opened upon lifting the cover 342, and yet the cover 342 may be reconnected to the container 322 by pressing the pressure sensitive adhesive 333 against the portion of the foil layer 344 that remained affixed to the flange.

The line of weakness 348 facilitates rupture of the foil layer 344 as the cover 342 is opened to help ensure that the foil layer 344 will tear along a predictable path without undue effort. As an option, the lines of weakness 348 may be deeper in front regions near the tab to enhance opening of the package.

Figure 10:
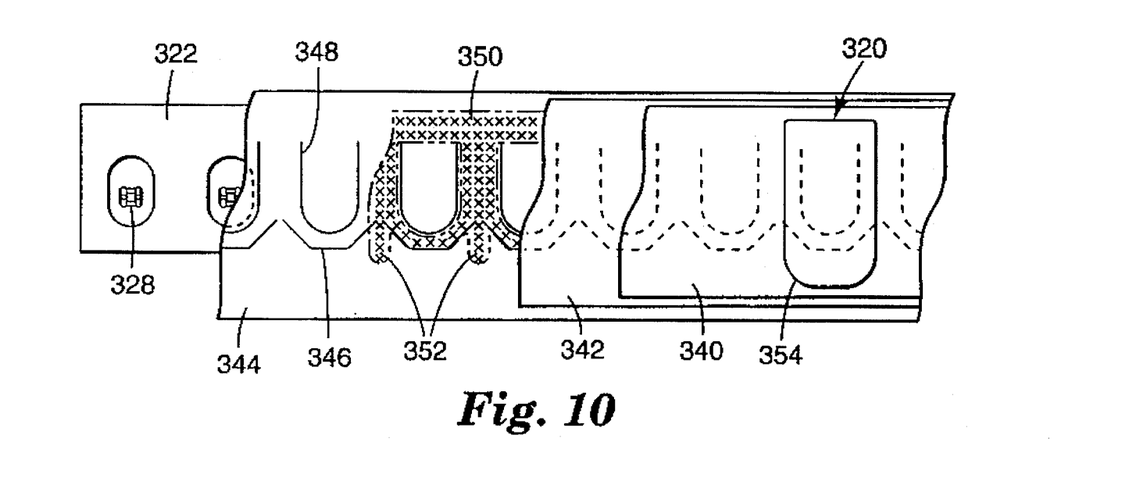
FIG. 10 is a plan view of a number of the articles shown in FIGS. 6–7 as they might appear during an intermediate manufacturing operation and before separated into individual containers, wherein portions of various layers used in constructing the articles have been cut away to facilitate understanding.

FIG. 10 is a depiction of an assembly of a number of articles 320 as the latter are constructed during manufacture. The aluminum foil layer 344 is heat sealed to the underlying container 322 before the cover 342 is applied to the aluminum foil layer 344. Once assembly is complete, individual articles 320 are separated from each other by cutting the assembly along the line 354.

In FIG. 10, the pattern of heat seal is represented by the crosshatching designated by the numeral 350. The portion of the foil layer 344 that is located forwardly of the line of weakness 346 is removed after the heat sealing operation has been completed. Optionally, the heat seal pattern 350 includes tamper evident indicator areas 352 that extend beyond the line of weakness 346. As the cover 342 is lifted from the container 322, the tamper evident indicator areas 352 detach from the flange and remain affixed to the overlying portion of the cover 342, so that one can determine if the container 322 has been opened.

Figure 11:
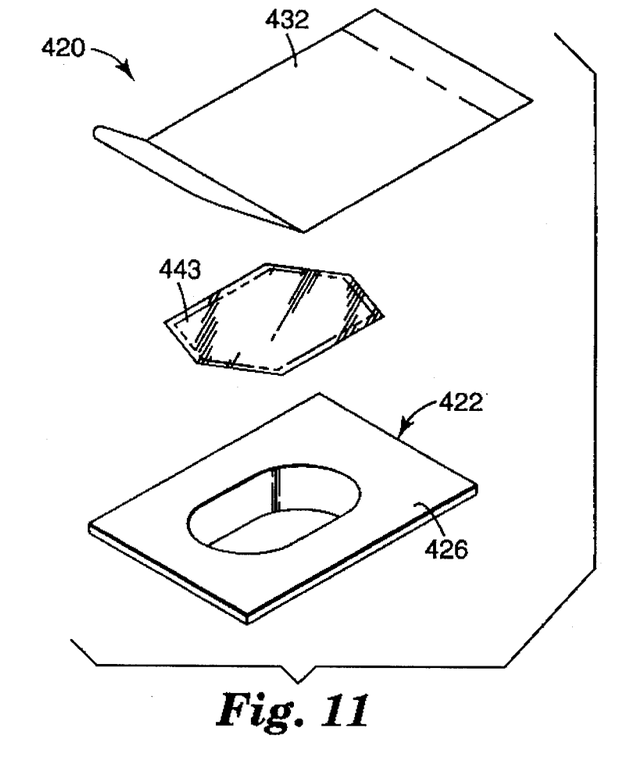
FIG. 11 is a view somewhat similar to FIG. 1 but illustrates another embodiment of the present invention.
Figure 12:
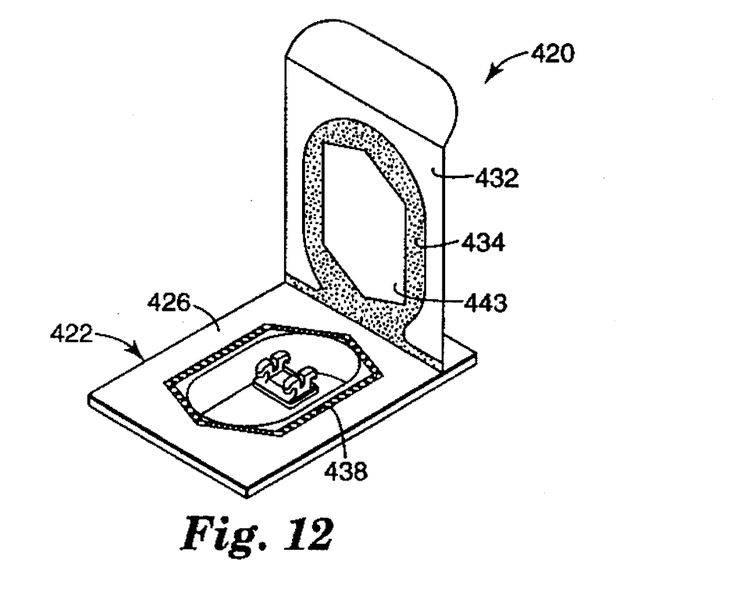
FIG. 12 is a view of the embodiment shown in FIG. 11 as it appears once it is assembled and after a cover has been opened.

Another embodiment of the invention is shown in FIGS. 11 and 12, and includes a packaged article 420 having a container 422 essentially identical to the container 22 mentioned above. A cover 432 of the article comprises a top film ("COMPUCAL II" brand, Flexcon Company, Inc., Spencer, Mass.; from ACUTEK of Inglewood, Calif., catalog no. ACTK 020) made of a 0.025 mm clear polyester film carrying an adhesive (no. 517, Flexcon) and covered by a printable matte topcoat, and an intermediate film made of a 0.13 mm polyester sheet having a metallized surface of aluminum bonded (by the no. 517 adhesive mentioned above) to the top clear polyester film. A double coated pressure sensitive adhesive assembly 434 (no. ACTK 023, Acutek) comprises a high tack, non-repositionable 0.018–0.02 mm thick layer of acrylic pressure sensitive adhesive (no. H529, Flexcon) bonded to the underside of the cover 432, a 0.025 mm thick polyester carrier film and a 0.018–0.02 mm thick layer of low tack, repositionable acrylic pressure sensitive adhesive (no. H558, Flexcon).

A generally hexagonal-shaped barrier film 443 is bonded to the low tack repositionable adhesive of the adhesive assembly 434 in a location extending over the well of the container 422 and along a portion of a flange 426 of the container 422 surrounding the well. The film 443 is made of PVDC (such as type "8", 46 gauge "SARAN WRAP" brand film, from Dow Chemical). The perimeter of the film 443 is heat sealed to the flange 26 along a second region 438.

When the cover 432 is raised to its open position as depicted in FIG. 12, the center of the relatively thin film 443 (i.e., the portion located inwardly of the phantom line shown on the film 443 in FIG. 11) is torn away from its heat-sealed periphery and remains affixed to the cover 443 to thereby expose the well. The cover 432 can be readily reclosed if desired by pressing the cover 432 against the flange 426 so that portions of the adhesive assembly 434 located outwardly of the heat-sealed portion of the film 443 are rebonded with underlying areas of the flange 426.

Optionally, the barrier film 443 initially may be part of an array of side-by-side, similarly-shaped hexagonal film sections that are integrally joined together along their sides. Such an array could be utilized in the manufacture of an assembly of a number of packaged articles 420 wherein an array of joined-together containers 422 and an array of joined-together covers 432 are also provided and subsequently cut apart into individual packaged articles 420 (in somewhat similar manner to the manufacturing method described in connection with FIG. 10). In such an instance, part or all of the film initially joining the film sections together could be removed if desired before the heat sealing operation.

The following example is given to illustrate, but not limit, the scope of this invention. Unless otherwise indicated, all percentages are by weight.

Example

A number of packaged articles were constructed according to FIGS. 1–3 and the accompanying description set out above. Each dental appliance 28 was a metal adhesive precoated orthodontic bracket (no. 2018–858, from 3M Unitek). For comparative purposes, a number of identical adhesive precoated orthodontic brackets were placed in prior art packages that are described in U.S. Pat. No. 5,350,059.

All of the packages were placed in an oven maintained at 60° C. After certain time intervals, fifteen packages according to the invention and fifteen prior art packages were opened. The concentration of EDMAB and CPQ remaining in the adhesive of each article was determined using a gas chromatograph and averaged.

The gas chromatographic column was from J & W Scientific (no. DB-5, 15 meter, 0.25 mm ID, 0.25 micron film). The gas chromatograph program was set to increase the column temperature from 50° C. to 300° C. at 10° per minute, and hold final temperature for five minutes. The injector conditions were as follows: 250° C., one microliter splitless injection, and a helium pressure of 10 psi. The detector was a flame ionization detector heated to 320° C.

Figure 13:
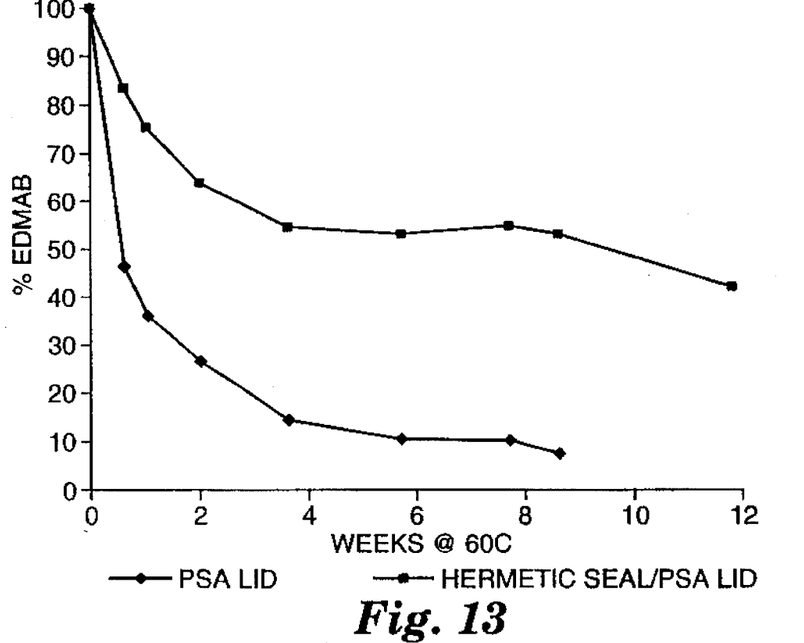
FIG. 13 is a graph depicting the loss of EDMAB from the adhesive over a period of time for the packaged article of the invention, as well as for a packaged article according to the prior art for comparative purposes.

A graphical depiction of the loss of EDMAB from the adhesive is illustrated in FIG. 13 for the adhesive 30 in the article 20 of the present invention (designated "HERMETIC SEAL/PSA LID"), as well as for the dental adhesive in the prior art packaged article (designated "PSA Lid"). The data in FIG. 13 show that EDMAB concentration decreased to about 42% of its original concentration after twelve weeks of accelerated aging in the packaged article of the present invention. By comparison, EDMAB concentration in the packaged article according to the prior art construction fell to about 7% of its original value after 8.6 weeks of accelerated aging. Thus, the packaged article 20 according to the present invention enabled the adhesive 30 to retain a significantly higher proportion of its original concentration of EDMAB over a period of time.

Figure 14:
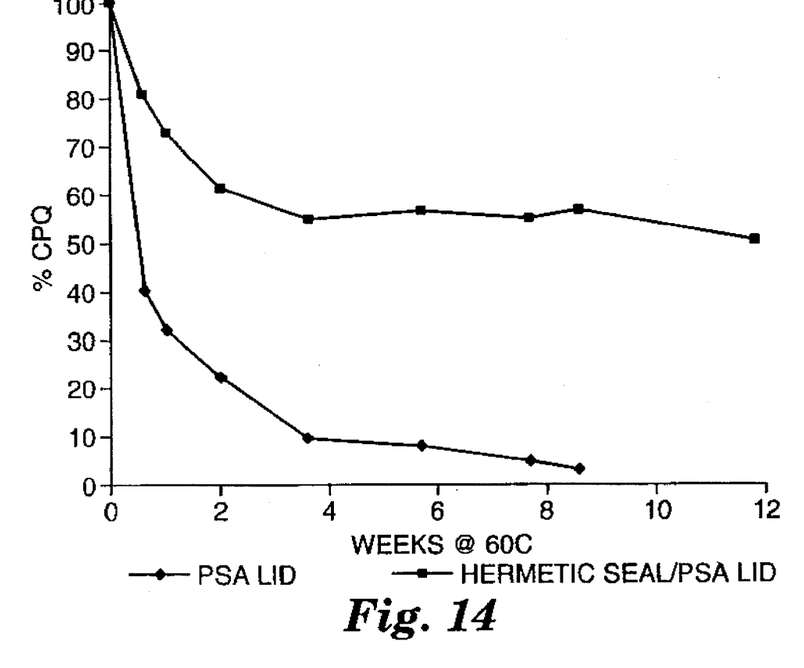
FIG. 14 is a graph somewhat similar to FIG. 13 except that FIG. 14 depicts the loss of CPQ from the adhesive over a period of time.

FIG. 14 is a graphical depiction somewhat similar to FIG. 13, except that FIG. 14 depicts loss of CPQ over the similar time intervals. The data in FIG. 14 show that the adhesive 30 of the article 20 of the present invention retained about 49.6% of its original concentration of CPQ after 11.8 weeks of accelerated aging. In contrast, the adhesive of the prior art packaged article retained about 3.2% of its original concentration of CPQ after 8.6 weeks of accelerated aging. Consequently, the present invention enabled the adhesive 30 to retain a substantially greater proportion of its original concentration of CPQ over an extended period of time.

Those skilled in the art will recognize that other modifications, additions or alternatives are possible without departing from the spirit of our invention. Accordingly, the invention should not be deemed limited by the specific embodiments set out above, but instead only by a fair scope of the claims that follow along with their equivalents.

We claim:

1. A packaged article containing:
    a container having a well with an opening and a flange surrounding said opening;
    a dental appliance having an exterior surface;
    an adhesive on said exterior surface, said adhesive including one or more volatile components;
    a cover extending over said opening and said flange;
    a pressure sensitive adhesive releasably connecting said cover to said flange along a first region at least partially surrounding said opening; and
    a hermetic seal connecting said cover to said flange along a second region surrounding said opening, said second region being located between said first region and said opening for substantially preventing at least a portion of said volatile components from contacting said pressure sensitive adhesive.

2. The packaged article of claim 1, wherein said second region has an annular configuration and extends entirely around said opening and said first region.

3. The packaged article of claim 1, wherein said hermetic seal includes a hot melt adhesive.

4. The packaged article of claim 1, wherein said hermetic seal is selected from the group consisting of an ultrasonic, radiant, impulse or induction seal.

5. The packaged article of claim 1, wherein said pressure sensitive adhesive comprises a repositionable adhesive.

6. The packaged article of claim 1, wherein said cover includes a layer of paper, and wherein said hermetic seal includes a layer of aluminum foil, and wherein said paper layer and said aluminum foil layer are laminated together.

7. The packaged article of claim 1, wherein said hermetic seal includes a barrier layer and a hot melt adhesive between said barrier layer and said flange.

8. The packaged article of claim 7, wherein said barrier layer includes one or more lines of weakness extending at least partially along said opening.

9. The packaged article of claim 7, wherein said barrier layer comprises aluminum foil.

10. The packaged article of claim 7, wherein said barrier layer comprises a polymeric material.

11. The packaged article of claim 7, wherein said barrier layer comprises metallized PVDC.

12. The packaged article of claim 7, wherein said barrier layer is separable from said container and said cover once said cover has been lifted from said opening for access into said well.

13. The packaged article of claim 1, wherein said first region consists essentially of two spaced apart sections that extend over said flange along opposite sides of said opening.

14. The packaged article of claim 1, wherein said volatile components include CPQ, and wherein the percentage weight loss of CPQ is less than 85% of its original weight when said appliance and said adhesive are retained in said well for a period of five weeks at 60° C.

15. The packaged article of claim 1, wherein said volatile components include CPQ, and wherein the percentage weight loss of CPQ is less than 60% of its original weight when said appliance and said adhesive are retained in said well for a period of five weeks at 60° C.

* * * * *